US00PP31836P2

(12) United States Plant Patent
Zary

(10) Patent No.: US PP31,836 P2
(45) Date of Patent: Jun. 2, 2020

(54) CRAPE MYRTLE PLANT NAMED 'GARZARNOBEWATER'

(50) Latin Name: *Lagerstroemia indica*
Varietal Denomination: GARzarnobewater

(71) Applicant: Early Morning LLC, Greendale, IN (US)

(72) Inventor: Keith W. Zary, Missoula, MT (US)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 16/602,341

(22) Filed: Sep. 17, 2019

(51) Int. Cl.
*A01H 5/00* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 5/00
See application file for complete search history.

*Primary Examiner* — Kent L Bell
(74) *Attorney, Agent, or Firm* — Barbara Campbell; Cochran Freund & Young LLC

(57) ABSTRACT

A new and distinct variety of crape myrtle plant, an upright, shrub having numerous flowers on panicles and resistance to leaf spot and powdery mildew strains found in Ohio and California, is disclosed.

2 Drawing Sheets

Genus and species: *Lagerstroemia indica.*
Denomination: 'GARzarnobewater'.

BACKGROUND

'GARzarnobewater' is a new and distinct variety of crape myrtle. 'GARzarnobewater' originated from a controlled cross in August 2010 in Tipp City, Ohio between the female parent, an unnamed and unpatented seedling derived from the cross between the crape myrtle plants 'Dynamite' (U.S. Plant Pat. No. 10,269) and 'Sacramento' (unpatented) and the male parent, an unnamed and unpatented seedling derived from the cross between the crape myrtle plants 'Dynamite' (U.S. Plant Pat. No. 10,269) and an unnamed and unpatented crape myrtle seedling.

The resulting seeds from the cross were collected in August 2010 and planted and evaluated in Tipp City, Ohio. 'GARzarnobewater' was selected in July 2011 from the population of seedlings in Tipp City, Ohio. 'GARzarnobewater' was first asexually propagated in July 2013 in Tipp City, Ohio from softwood cuttings.

Other subsequent asexual propagations were conducted in controlled environments in Tipp City, Ohio and demonstrate that 'GARzarnobewater' reproduces true to type in successive generations of asexual reproduction via softwood cuttings.

SUMMARY

The following are the most outstanding and distinguishing characteristics of this new variety when grown under normal horticultural practices in Tipp City, Ohio.

1. An upright, shrub having numerous flowers on panicles; and
2. Resistance to leaf spot and powdery mildew strains found in Ohio and California.

DESCRIPTION OF THE PHOTOGRAPHS

This new crape myrtle plant is illustrated by the accompanying photographs which show the plant's overall plant habit including form, foliage, and flowers. The photographs are of a 4-year old plant grown outdoors in Tipp City, Ohio in August 2019. The colors shown are as true as can be reasonably obtained by conventional photographic procedures.

DETAILED DESCRIPTION

Figure 1:
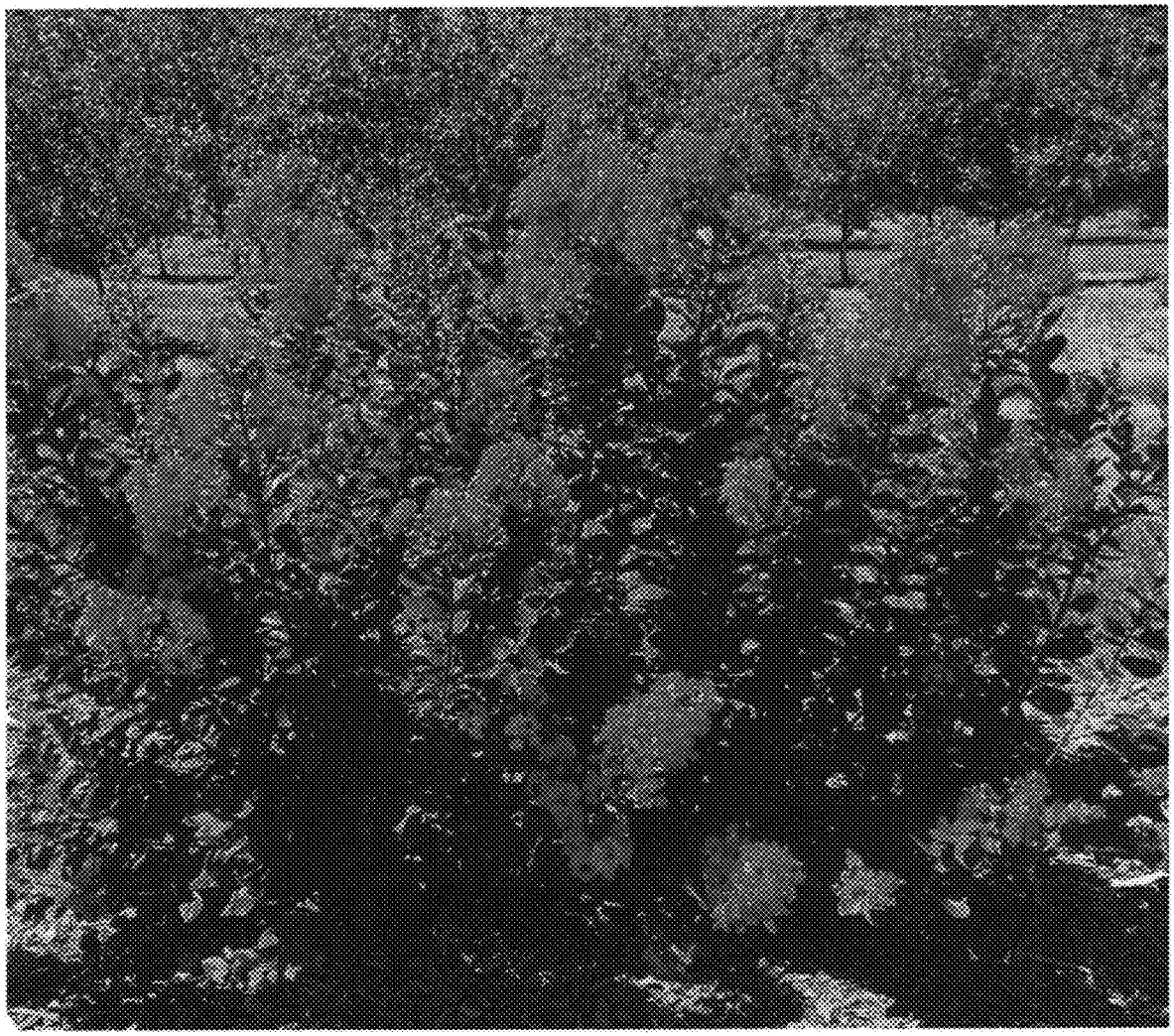
FIG. 1 shows the overall plant habit of 'GARzarnobewater'.
Figure 2:
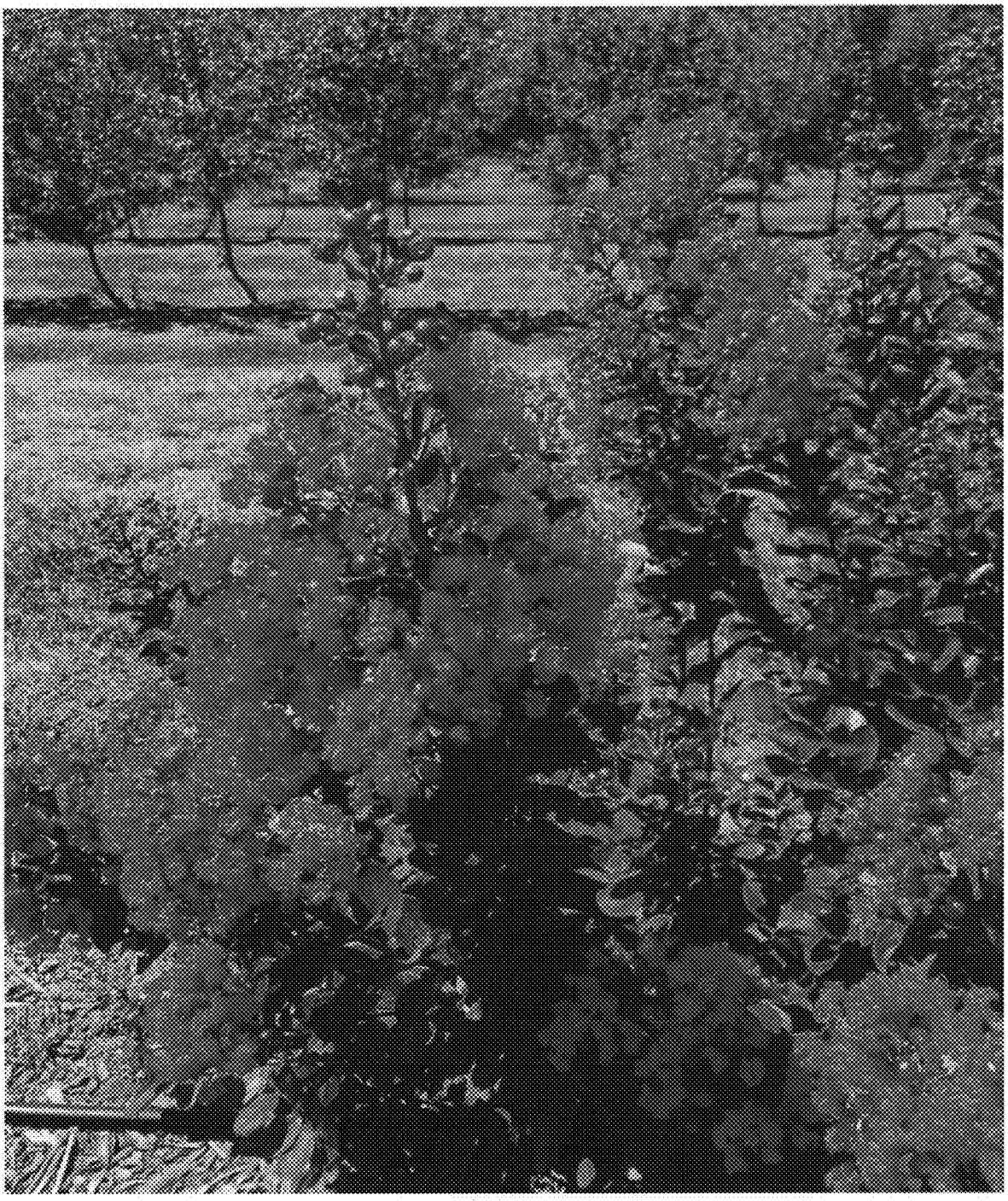
FIG. 2 shows a close-up of the individual flowers, buds, foliage, and bark of the plant.

The following detailed descriptions set for the distinctive characteristics of 'GARzarnobewater'. The data which define these characteristics were collected outdoors in Tipp City, Ohio. Plants were propagated in a greenhouse in 2014 and transplanted to an outdoor field in Tipp City, Ohio in May 2015 and evaluated each year thereafter. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:

*Family.*—Lythraceae.
*Species.*—*Lagerstroemia indica.*
*Variety.*—'GARzarnobewater'.

Parentage:

*Female parent.*—An unnamed and unpatented seedling derived from the cross between the crape myrtle plants 'Dynamite' (U.S. Plant Pat. No. 10,269) and 'Sacramento' (unpatented).

*Male parent.*—An unnamed and unpatented seedling derived from the cross between the crape myrtle plants 'Dynamite' (U.S. Plant Pat. No. 10,269) and an unnamed and unpatented crape myrtle seedling.

Propagation:
*Type*.—Softwood cuttings.
*Time to initiate roots*.—Three weeks.
*Time to produce a rooted young plant*.—8 to 10 weeks after propagation.
*Root description and habit*.—Fine, fibrous, well-branched, and RHS 177B (Greyed-Orange).

Plant description:
*Plant form and growth habit*.—Upright and well-branched.
*Branching habit*.—Free-branching.
*Plant height*.—95.0 cm.
*Plant diameter* (*area of spread*).—85.0 cm.

Lateral branch description:
*Length*.—50.0 cm to 60.0 cm.
*Diameter*.—0.5 cm halfway up the lateral stem; 1.0 cm to 1.1 cm at the base; four longitudinal carinae along either side of petioles.
*Internode length*.—1.4 cm.
*Strength*.—Strong.
*Texture, immature*.—Smooth.
*Texture, mature*.—Exfoliating bark.
*Color, immature*.—RHS 181A (Greyed-Orange).
*Color, mature*.—RHS 165A (Greyed-Orange).

Bark:
*Immature stem color*.—RHS 181A (Greyed-Orange).
*Mature stem color*.—RHS 165A (Greyed-Orange).

Leaf:
*Arrangement*.—Sub-opposite to alternate.
*Length*.—7.2 cm.
*Width*.—3.5 cm.
*Shape*.—Ovate.
*Apex*.—Acuminate.
*Base*.—Rounded to cuneate.
*Margin*.—Ciliolate.
*Texture*.—Upper surface: Lustrous, glabrous, leathery. Lower surface: Lustrous, glabrous.
*Venation pattern*.—Pinnate.
*Venation color*.—Upper surface: RHS 146B. Lower surface: RHS 146C.
*Immature leaf color*.—Upper surface: RHS 187A (Greyed-Purple). Lower surface: RHS 146A (Yellow-Green).
*Mature leaf color*.—Upper surface: RHS 136C (Green). Lower surface: RHS 137B (Green).
*Petioles*.—Length: 3.0 mm. Width: 2.0 mm. Color: RHS 146B (Yellow-Green). Texture: Puberulent.

Flower:
*Flower arrangement and flowering habit*.—Flowers on panicles; flowers on the terminal main shoots first and then on developing laterals at their terminals; large terminal panicle will have 80 to 100 flowers; smaller lateral panicles will have 15 to 20 flowers.
*Natural flowering season and flower longevity*.—Mid to late summer into early fall; blooms for six or more weeks in Ohio; in California, if the plant is cut back, the plant will rebloom in 6 to 7 weeks.
*Fragrance*.—Little to none.
*Inflorescence height*.—For the terminal main shoot, 15.0 cm to 18.0 cm.
*Inflorescence diameter*.—11.0 cm to 12.0 cm.
*Flower diameter*.—3.2 cm.
*Flower length*.—1.7 cm.
*Flower buds*.—Globose; smooth; 7.0 mm length and 7.0 mm wide; base is rounded and the apex is slightly cuspidate; color is RHS 181A.
*Flower bud color*.—RHS 181A.

Petals:
*Quantity*.—6 per flower.
*Lobe length*.—1.7 cm.
*Lobe width*.—1.0 cm.
*Lobe shape*.—Ruffled.
*Apex*.—Rounded.
*Base*.—Sagittate to cordate.
*Margin*.—Crisped.
*Texture* (*both upper and lower surfaces*).—Soft and ruffled.
*Color* (*both upper and lower surfaces*).—RHS 59C.

Sepals:
*Quantity and arrangement*.—6 and fused at the base.
*Length*.—Above the fused portion, the length is 4.0 mm.
*Width*.—Above the fused portion, the width is 6.0 mm.
*Shape*.—Triangular.
*Apex*.—Acute.
*Base*.—Fused.
*Margin*.—Entire.
*Color*.—Upper surface: RHS 147C. Lower surface: RHS 145D.

Peduncles:
*Length*.—12.0 cm and 15.0 cm.
*Diameter*.—3.0 mm to 4.0 mm.
*Strength*.—Strong and rigid.
*Texture*.—Rough.
*Color*.—RHS 183D.

Pedicels:
*Length*.—5.0 mm to 6.0 mm.
*Diameter*.—1.0 mm.
*Strength*.—Strong.
*Texture*.—Smooth.
*Color*.—RHS 138D.

Reproductive organs:
*Androecium*.—Quantity of stamens per flower: About 30; composed of a mixture of shorter and longer stamens. Filament length: The long stamens have a filament length of 12.0 mm to 13.0 mm and the shorter stamens have a filament length of 8.0 mm to 10.0 mm. Anther shape: Somewhat flattened ellipsoid. Anther length: 1.0 mm to 1.2 mm. Anther color: RHS 183D. Amount of pollen: Abundant, especially on the longer stamens. Pollen color: RHS 18C.
*Gynoecium*.—Quantity of pistils per flower: 1. Pistil length: 6.0 mm to 7.0 mm or if stretched, to 2.2 cm. Style length: 7.0 mm to 8.0 mm. Style color: RHS 183C. Stigma color: RHS 200D. Stigma shape: Globose. Ovary color: RHS 1C.

Fruit and seed set: Seed is present; it is lunate to lanceolate samara in shape, a 6-valved dehiscent capsule that is about 2.3 mm wide and 7.0 mm in length; color is RHS 199C to RHS 199D.

Disease and insect resistance: Resistant to powdery mildew strains *Erysiph* found in Ohio and California and resistant to leaf spot, *Cercospora*.

COMPARISON WITH PARENTAL AND COMMERCIAL LINES

Table 1 shows a comparison of differences between 'GARzarnobewater' and both parental lines.

TABLE 1

| Comparison with Parental Lines | | | |
|---|---|---|---|
| Characteristic | 'GARzarnobewater' | Female parent, un-named crape myrtle seedling | Male parent, un-named crape myrtle seedling |
| Flower color | RHS 59C (Red-Purple) | RHS 52A | RHS 20C (Red-Purple) |
| Plant habit and size | Upright shrub, up to 95.0 cm in height | Upright small tree, up to 3 m in height | Upright shrub, up to 1.5 m in height |

Table 2 shows a comparison of the differences between 'GARzarnobewater' and the commercial crape myrtle variety 'Cherry Mocha' (U.S. Plant Pat. No. 28,281).

TABLE 2

| Comparison with Commercial Line | | |
|---|---|---|
| Characteristic | 'GARzarnobewater' | 'Cherry Mocha' |
| Flower color | RHS 59C | RHS 60B |
| Plant habit and size | Upright shrub, 95 cm by 85 cm | Upright shrub, 85 cm by 75 cm |

I claim:

1. A new and distinct variety of crape myrtle plant designated 'GARzarnobewater' as illustrated and described herein.

* * * * *